United States Patent [19]

Takahashi et al.

[11] 4,296,219

[45] Oct. 20, 1981

[54] BISMIDE-ETHER COMPOUNDS, COMPOSITIONS THEREOF, AND METHOD OF PRODUCING SAME

[75] Inventors: Akio Takahashi; Yutaka Itoh; Motoyo Wajima; Hirosada Morishita; Akio Nishikawa, all of Ibaraki, Japan

[73] Assignees: Hitachi, Ltd.; Hitachi Chemical Co., Ltd., both of Tokyo, Japan

[21] Appl. No.: 5,233

[22] Filed: Jan. 22, 1979

[30] Foreign Application Priority Data

Mar. 31, 1978 [JP] Japan .................................. 53-36592
Jun. 7, 1978 [JP] Japan .................................. 53-67712

[51] Int. Cl.³ ............................................ C08G 73/12
[52] U.S. Cl. .................................... 525/488; 525/502; 528/176; 528/183; 260/326.26; 260/239.3 R; 546/193; 546/194; 546/208
[58] Field of Search ................ 525/488, 502; 528/176, 528/183

[56] References Cited

U.S. PATENT DOCUMENTS

| | | |
|---|---|---|
| 3,838,097 | 9/1974 | Wirth et al. ......................... 528/170 |
| 3,868,351 | 2/1975 | Hand et al. ......................... 528/183 |
| 3,886,119 | 5/1975 | D'Alelio ............................. 528/87 |
| 4,026,871 | 5/1977 | D'Alelio ............................. 528/170 |
| 4,038,251 | 7/1977 | Forgo et al. ......................... 528/170 |
| 4,127,615 | 11/1978 | Zahir et al. ......................... 525/502 |

FOREIGN PATENT DOCUMENTS

| | | |
|---|---|---|
| 506535 | 10/1954 | Canada .......................... 260/326.26 |
| 2437286 | 4/1975 | Fed. Rep. of Germany . |
| 2459925 | 7/1975 | Fed. Rep. of Germany ...... 528/170 |
| 2459961 | 7/1975 | Fed. Rep. of Germany . |
| 1463300 | 2/1977 | United Kingdom . |
| 1480072 | 7/1977 | United Kingdom . |

Primary Examiner—Edward M. Woodberry
Attorney, Agent, or Firm—Craig and Antonelli

[57] ABSTRACT

A bisimide-ether compound having the general formula is obtained by reacting an ethylenically unsaturated dicarboxylic acid anhydride, a diamine compound and a phenolic compound having in the molecule at least two hydroxyl groups, or by reacting a prepolymer of the anhydride and diamine compound with the phenolic compound:

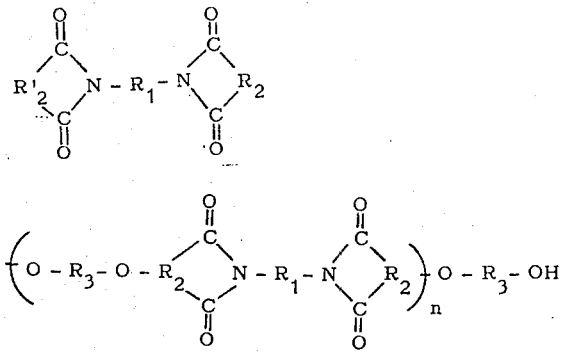

wherein $R_1$ is a group containing at least two carbon atoms, $R_2$ is a group containing at least two carbon atoms, $R'_2$ is a group containing at least two carbon atoms and a carbon-carbon double bond, $R_3$ is an aromatic group, the nitrogen atoms of the imide rings being directly connected to different carbon atoms of the group $R_1$, the carbonyl groups of the imide rings being directly connected to different carbon atoms of the group $R_2$ or $R'_2$, the oxygen atoms between the groups $R_2$ and $R_3$ being directly connected to an aromatic nucleus of the group $R_3$, and n is an integer of zero, one or more than 1.

40 Claims, No Drawings

BISMIDE-ETHER COMPOUNDS, COMPOSITIONS THEREOF, AND METHOD OF PRODUCING SAME

The present invention relates to a new solvent-soluble bisimideether compound or resin and resin compositions containing the new bisimideether compound or resin, which can provide a heat resistant thermoset resin. The new compound and thermosetting resin is featured by good solvent solubility to low boiling-point solvents such as acetone and ketone and by providing a thermoset resin having excellent heat resistant properties.

There are various kinds of heat resistant thermost resins such as polyimide resin. This resin needs a high temperature to cure the corresponding curable composition. The polyimide resin has another drawback that the composition produces water as a by-product upon heating to cyclize to introduce imide rings into the molecule. The drawbacks may be solved by aminobismaleimide resins. The latter needs, however, high boiling-point solvents, such as N-methyl-2-pyrrolidone an N,N'-dimethylformamide, because of its poor solubility. Therefore, it is difficult to completely remove the high boiling-point solvents using conventional equipments, and the cured resins showed poorer heat-resistant properties due to the remaining solvent than the polyimide resin.

Epoxy-modified polyimide resins are disclosed in Japanese laid-open print No. 5 51499 to 1977 and in Japanese Publication No. 3,7678 of 1976. Triazine polymers are also known in the art. These known polymers exhibit unsatisfactory heat-resistant properties and, in particular, the epoxy-modified polyimide resin has poor unflammability.

On the other hand, Japanese laid-open print No. 145456 of 1977 discloses polyimide resins which are obtained by reacting a heat-fusible aniline-modified phenol resin with an unsaturated bisimide. The aniline-modified phenol resin is prepared by reacting in the absence of a catalyst phenols with anhydroformaldehyde.

According to experiments conducted by the present inventors the polyimide resins exhibit insufficient heat-resistant properties, and the production of the aniline-modified phenol resins needs a complicated process for removing by-products and unreacted components in vacuum, which results in increasing a production cost of the polyimide resins.

SUMMARY OF THE INVENTION

It is an object of the present invention to provide a bisimide-ether compound or resin, which is well soluble even in low boiling-point solvents.

It is another object of the present invention to provide a thermosetting resin composition containing the bisimide-ether compound producible in a simple method.

It is still another object of the present invention is provide a solvent-soluble thermosetting resin composition containing the bisimide-ether compound or resin, which has good curing characteristics.

It is still another object of the present invention to provide a thermosetting resin composition capable of providing a thermoset resin which has an improved adhesion to other material such as glass cloth.

It is further still another object of the present invention to provide methods of producing the solvent-soluble bisimide-ether compound or resin and of producing the solvent soluble thermosetting resin compositions.

According to the present invention, there is provided a solvent-soluble bisimide-ether compound resin having the general formula:

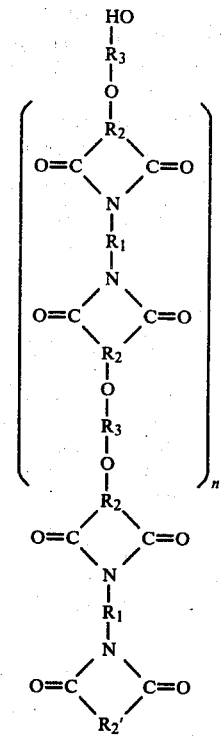

wherein $R_1$ is a group containing at least two carbon atoms, preferably less than 20 carbon atoms, the nitrogen atoms of the imide rings being directly connected to different carbon atoms of the group $R_1$, $R_2$ is a group having at least two carbon atoms, preferably 2 to 6 carbon atoms, the carbonyl group of the imide rings being directly connected to different carbon atoms of the group $R_2$ or $R'_2$, $R'_2$ is a group containing at least two carbon atoms, preferably 2 to 6 carbon atoms, and a carbon-carbon double bond, $R_3$ is an aromatic groups containing at least one aromatic nucleus, preferably 1 to 20 nuclei, the oxygen atoms between the groups $R_2$ and $R_3$ being directly connected to different carbon atoms of the aromatic nucleus, and n is an integer of zero, one or larger than 1. When $R_3$ is a residual group of phenol resins such as phenol novolac resins, the bisimide-ether compound is resinous. The value of "n" is within a range such that the bisimide-ether compound is soluble to form a solution of at least 50% concentration in an organic solvent having a boiling point lower than 130° C. at normal temperature under normal pressure. Preferably, the number of "n" is less than 10.

The present invention also provides a thermosetting resin composition containing at least 10% by weight of the above-mentioned bisimide-ether compound or resin and further provides thermosetting resin compositions mixed with various kinds of ingredients.

In the present invention, by the term "thermosetting" is meant that a resin or composition containing same is curable upon heating in the presence or absence of a catalyst or hardener.

The present invention further provides methods of producing the above-mentioned bisimide-ether compound or resin in which an ethylenically unsaturated dicarboxylic acid anhydride and a diamine compound are reacted in the presence of an aromatic compound having in the molecule at least two phenolic hydroxyl groups, or in which a bisimide compound having two carbon-carbon double bonds in the molecule is reacted with an aromatic compound having in the molecule at least two phenolic hydroxyl groups.

The above objects and other objects and features of the present invention will be apparent from the following detailed description of the present invention.

DETAILED DESCRIPTION OF THE INVENTION

(1) Ethylenically unsaturated dicarboxylic acid anhydride

Various kinds of dicarboxylic acids are usable as one of the reactants for desired bisimide-ether compounds of the present invention. From the practical point of view, anhydrides of dicarboxylic acids are prefereable. Examples of dicarboxylic acid anhydrides are maleic acid anhydride, citraconic acid anhydride, itaconic acid anhydride, dichloromaleic acide anhydride, Diels-Alder adducts of these anhydrides and cyclodienes. These anhydrides are used singly or in combination. Among the above anhydrides is most preferable maleic acid anhydride because of high reactivity of carbon-carbon double bonds with hydroxyl groups of the aromatic compound.

(2) Diamine Compounds

Diamine compounds have at least two carbon atoms. That is, the compounds have in the molecule a normal chain or branched chain of an alkylene group, a cycloalkylene group containing 5 to 6 carbon atoms, heterocyclic groups of 4 to 6 membered ring containing at least one atom of oxygen, nitrogen, sulfur, phenylene groups, polyaromatic groups, or arylene groups bridged by —COO—, —SO$_2$—, —O—, or —N=N—. The number of the aromatic nuclei of the polyaromatic groups is preferably one to four.

Examples of diamine compounds include 4,4-diaminodicyclohexyl methane, 1,4-diaminocyclohexane, 2,6-diaminopyridine, m-phenylenediamine, p-phenylenediamine, 4,4'-diaminodiphenylmethane, 2,2'-bis (4-aminophenyl)propane, bendizine, 4,4'-diaminophenyloxide, 4,4'-diaminodiphenyl sulfone, bis(4-aminophenyl)methylphosphine oxide, bis(4-aminophenyl)methylamine, 1,5-diaminonaphthlene, m-xylylenediamine, p-xylylenediamine, hexamethylenediamine, 6,6'-diamine-2,2'-dipyridyl, 4,4'-diaminobenzophenone, 4,4'-diaminoazobenzene, bis(4-aminophenyl)phenylmethane, 1,1'-bis(4-aminophenyl)cyclohexane, 2,5-bis(m-aminophenyl)thiazoro(4,5-d)thiazole, 5,5'-di(m-aminophenyl)(2,2')-bis(1,3,4-oxadiazorile), 4,4'-diaminodiphenylether, 4,4'-bis(p-aminophenyl)-2,2'-dithiazole, m-bis(4-p-aminophenyl-2-thiazorile)benzene, 4,4'-diaminobenzanilide, 4,4'-diaminophenylbenzoate, N,N'-bis(4-aminobenzyl)-p-phenylene diamine, and 4,4'-methylene bis(2-chloroaniline). These diamines are used singly or in combination. Among the diamine compounds are preferable aromatic diamines when particularly excellent heat resistant properties are required for the resulting thermoset resins.

With regard to a ratio of the diamine to anhydride, there is almost to critical limit as long as curing characteritics of a thermosetting resin is concerned. From the view points of heat-resistant properties and non-flammability 0.3 to 2 moles of a diamine to one mole of an anhydride is preferable. When a bisimide-ether polymer having specific recurrent units is desired or a bisimide prepolymer having the following general formula is required, one mole of a diamine to two moles of an anhydride is preferable. Around the ratio of 1 mole of diamine to 2 moles of anhydride, one of the components may be used in slight excess. Even when a diamine is used in large excess, an unreacted part of the diamine can be acted as a hardener of a mixture containing the bisimide-ether polymer.

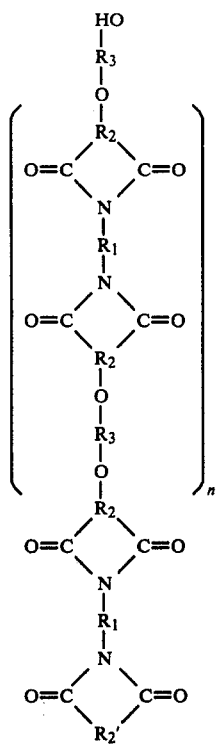

In the formula above, the group R$_3$ may have the following recurring units when phenol resins are used:

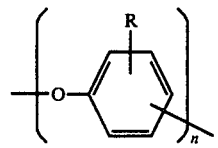

wherein n is 1 to 20, and R is methyl group. One or two R can be attached to the nucleus.

(3) Aromatic compounds having phenolic hydroxyl groups

One aspect of the present invention resides in that a dicarboxylic acid anhydride and a diamine compound are reacted in an aromatic compounds having phenolic hydroxyl groups, whereby the reaction takes place in the absence of any solvent. That is, since the anhydride and diamine are soluble in the aromatic compound, the mixture can be reacted without any solvent.

The aromatic compounds having phenolic hydroxyl groups (hereinafter referred to as a phenolic compound for simplicity) include monomeric and polymeric compounds. In order to carry out the reaction between the anhydride and diamine and the phenolic compound, the phenolic compounds having a melting point or a softening point lower than 170° C. are used. The reaction temperature is lower than 200° C., preferably 100° to 180° C. By dissolving a diamine compound in a phenolic resin, the softening point of the phenol resin can considerably be lowered. Therefore, phenol resins having a softening point not higher than 170° C. can be used not only as a reactive component but also as a solvent in the present invention.

A range of molecular weight of phenol resins is preferably within about zoo to about 2500.

Examples of starting materials for phenol resins include phenol, o-cresol, m-cresol, p-cresol, 2,5-xylenol, 3,4-xylenol, 2,6-xylenol, o-chlorophenol, m-chlorophenol, p-chlorophenol, o-phenylphenol, m-phenylphenol, p-phenylphenol, saligenin (salicyl alcohol) and biephenol A. Phenol resins are obtained by reacting the above mentioned compounds with formaline or paraformaldehyde in the presence of acidic or basic catalysts.

Other examples of phenol resins are diphenyl ether resin polymer, xylene-modified phenol resin polymer, parahydroxypolystyrene resin polymer, brominated parahydrolxypolystyrene resin polymer, and bisphenol A-furfural resin polymer. Monomeric compounds having at least two hydroxyl groups are also useful, which include bisphenol A, resorcinol, catecol, and hydroquinone.

A ratio of the phenol compound to anhydride and diamine may vary in a wide range. From the practical point of view, the phenol compound is within a range of 30 to 70% by weight based on the total weight of the phenol compound, anhydride and diamine.

When a bisimide prepolymer is used in place of the anhydride and diamine, the ratio of the phenolic compound may also vary in a wide range, while an equivalent molar ratio of the two components may be preferable to produce a desired bisimide-ether polymer with high yield.

(4) Bisimide prepolymer

Bisimide prepolymers used in the present invention are represented by the general formula:

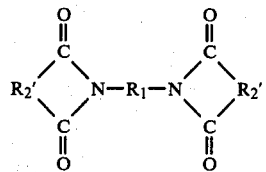

wherein $R_1$ is a group containing at least two carbon atoms preferably less than 20 carbon atoms and $R'_2$ is an unsaturated group containing a carbon-carbon double bond and containing at least two carbon atoms, preferably less than 20 carbon atoms. The nitrogen atoms of the imide rings are directly connected to different carbon atoms of the group $R_1$ and the carbonyl groups of the imide rings are directly connected to different carbon atoms of the group $R'_2$.

The group $R_1$ is a residual group of a diamine compound and can be a normal or branched chain of alkylene group having 2 to 10 carbon atoms, a cyclic alkylene group containing 5 to 6 carbon atoms, a heterocyclic group of 4 to 6 membered ring containing 2 to 5 carbon atoms and at least one atom of oxygen, nitrogen, and sulfur, a phenylene group, and a polyaromatic group. These groups may contain one or more functional or non-functional groups such as carboxyl groups (3,3'-dicarboxyl-4,4'-diaminodiphenyl methane), halogen atoms (3,3'-dichloro-4,4'-diaminodiphenyl methane) or amido groups (4,4'-diamino diphenyl ether-6-amido), provided that the latter groups do not cause undesirable effects on the production of the thermosetting resin of the present invention. The functional groups may react when the thermosetting resin of the present invention is further reacted with other components or is cured by heating.

The groups may be polyarylene groups in which aromatic nuclei are bridged by —COO—, —SO₂—, —O—, —N=N— or the like.

The group $R_2$ is a residual group of a dicarboxylic acid or its anhydride. Examples of unsaturated bisimides used in the present invention include N,N'-ethylenediamaleimide, N,N'-hexamethylenedimaleimide, N,N'-m-phenylenedimaleimide, N,N'-p-phenylenedimaleimide, N,N'-m-xylylene-dimaleimide, N,N'-oxy-di-p-phenylenedimaleimide, N,N'-methylenebis (3-chloro-p-phenylene)dimaleimide, N,N'-sulfonyldi (p-phenylene)dimaleimide, N,N'-methylene (4, 1-cyclohexylene)dimaleimide, and N,N'-cyclohexylidene di(p-phenylene)dimaleimide.

A preferable ratio of the unsaturated bisimide prepolymer to the phenol compound is within a range of 1:2 to 2:1 in terms of the ratio of carbon-carbon double bonds to the number of hydroxyl groups. The preferable reaction conditions for the components are 100° to 180° C. for 5 to 120 minutes.

(5) Hardeners and catalysts

The thermosetting resins and thermosetting resin compositions may optionally be mixed with a hardener or a curing catalyst. As a hardener there are various kinds of amine compounds which include, for example, 4,4'-methylene bis(2-chloroaniline), 4,4'-methylene bis (2,5-dichloroaniline), 4,4'-methylenedianiline, 4,4'-oxydianiline, 3,3'-sulfonyldianiline, m-phenylenediamine, diethylaniline, ethylenediamine, diethylenetriamine, triethylenetetramine, and dicyanodiamide.

When a mixture of dicarboxylic acid anhydride, diamine and phenol compound is used as a starting material, and when an excess amount of diamine with respect to anhydride is used, the addition of the amine compound is not necessary. On the other hand, a mixture of bisimide prepolymer and phenol compound is used, the addition of amine compound to the B-stage resin or the mixture is recommendable. The addition of the amine compound to the B-stage resin is most preferable. A practically useful amount of the amine compound is within a range of 5 to 10% by weight based on the resin components.

As a curing catalyst imidazoles and derivatives thereof can be added to the mixture or B-stage resin of the present invention. A practical amount of imidazoles is within a range of 0.1 to 2% by weight based on the resin components. Examples of imidazoles include 2-methyl imidazole, 2-ethyl-4-methylimidazole, 2-phenylimidazole, 2-undecaimidazole, 2-ethylimidazole, 2,4-dimethylimidazole, 2-isopropylimidazole, azine adducts of the imidazole, trimellitic acid salts of the imidazoles, and nitrylethyl adducts of the imidazoles.

When the termosetting resins of the present invention are mixed with epoxy resin, hardeners or curing catalysts for epoxy resins may also be added.

(6) Epoxy resins

The thermosetting resins or compositions of the present invention can be mixed with epoxy resins to improve adhesiveness of thermoset resins or to modify chemical or physical properties of the thermoset resins.

Epoxy resins having in the molecule at least two epoxy groups include, for example, glycidyl ether of bisphenol A, 3,4-epoxycyclohexylmethyl-3,4-epoxycyclohexanecarboxylate, 4,4'-(1,2-epoxyethyl)bisphenyl, 4,4'-di(1,2-epoxyethyl)diphenylether, resorcineglycidylether, bis(2,3-epoxycyclopentyl)ether, N,N'-m-phenylene bis(4,5-epoxy-1, 2-cyclohexane-dicarboxyimide), triglycidyl compound of p-aminophenol, 1,3,5-tril(1,2-epoxyethyl)benzene, tetraglycidoxytetraphenylmethane, and polyglycidylether of phenolformaldehyde novlac resin.

An amount of epoxy resins is within a range of 5 to 70%, preferably 10 to 50% by weight based on the total resin components. The epoxy resins can be mixed with mixture of a bisimide prepolymer and phenol compound or with a reaction product of a mixture of the bisimide prepolymer and phenol compound or a reaction product of a mixture of an anhydride, diamine and phenol compound.

(7) Reaction mechanisms (i) Reaction between anhydride, diamine and phenol compound When a mixture of the three components are heated at 100° to 180° C. under anhydrous condition, a bisimide-ether compound or resin is formed in the reaction product. While the yield of the polymer depends on the reaction conditions and starting materials used, about 10% or more of the reaction product is produced in the B-stage reaction product. Although the reaction mechanisms have not been elucidated, it is speculated that the following reactions take place.

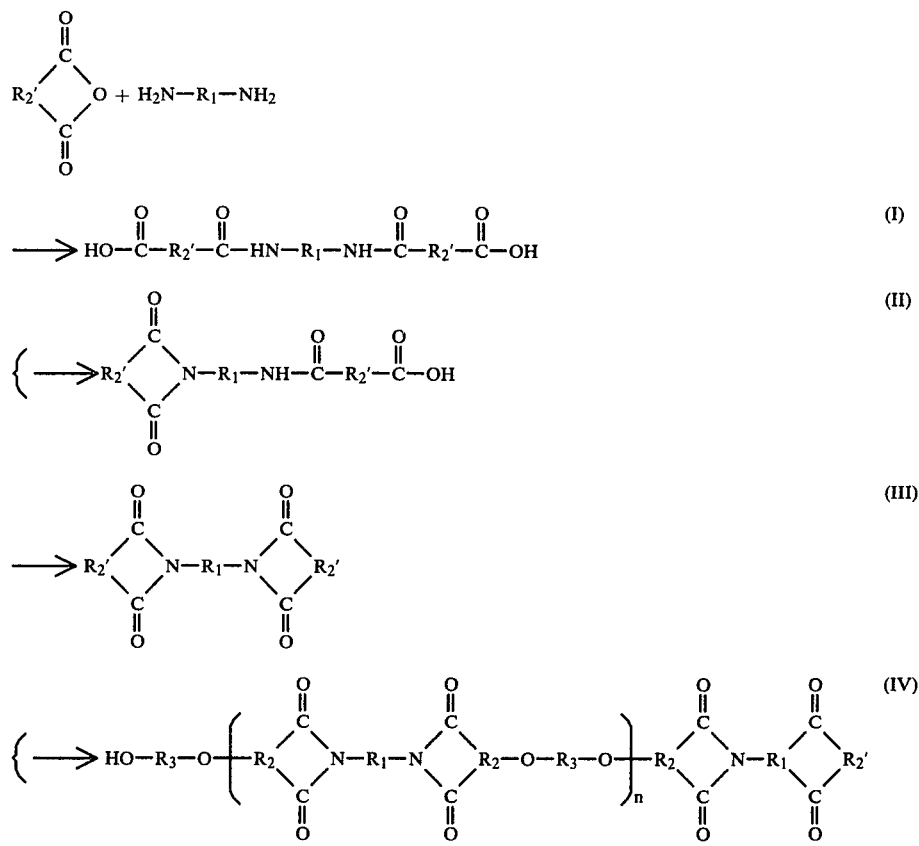

The reactions (II) and (III) may be coexistent in the reaction system. The reaction (IV) is a result of addition reaction of a phenol compound to a carbon-carbon double bond of the group R'$_2$ during the reactions (I)—(III) or after the reaction (III).

The addition reaction may be illustrated as follows:

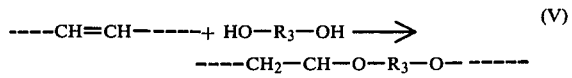

(V)

There may occur various by-reactions in the reaction system. For example, addition reaction of an amino group to carbon-carbon double bond may occur.

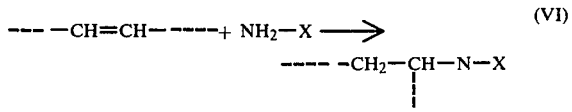

(VI)

This addition reaction tends to occur, particularly when diamine compound is used in largely excess to anhydride. In the reaction (VI) X designates a residue of diamine compound or of various intermediates such as amide acids, or imide.

Cross-linking reaction by radical polymerization of carbon-carbon double bonds may occur when the reaction temperatures are excessively high.

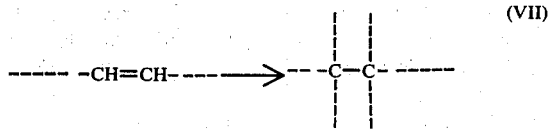

(VII)

The cross-linking reaction is undesirable for producing a bisimide-ether compound or a solvent-soluble thermosetting resin of the present invention, because the cross-linking reaction lessens the solubility of the reaction product.

When the bisimide-ether compound or a resin composition containing the bisimide-ether compound is heated in the presence or absence of a proper curing catalyst or a hardener, the bisimide-ether compound is further polymerized, particularly when there remain a sufficient amount of double bonds in $R'_2$ groups, to become a macromolecular thermost resin of network structure. In order to produce thermoset resins having excellent heat resistant properties, phenol compounds having in the molecule more than two hydroxyl groups are used. In this case, the group $R_3$ in the bisimide-ether compound contains more than one free hydroxyl group directly connected to an aromatic nucleus.

The bisimide-ether compound or compositions containing the same can be obtained by heating the mixtures at a temperature higher than 80° C., preferably 100° to 180° C. for 5 to 300 minutes. The resulting bisimide-ether compound or resin, is soluble even in low boiling-point solvents such as methyl ethyl ketone or acetone. It was found that the reaction product can form a solution containing 50% or more of the bisimide-ether compound in the low boiling-point solvents.

(ii) Reaction between bisimide prepolymer and phenol compound

When a bisimide prepolymer is heated in the presence of a phenol compound, the following reactions may take place. For convenience, the following example is shown by bismaleimide.

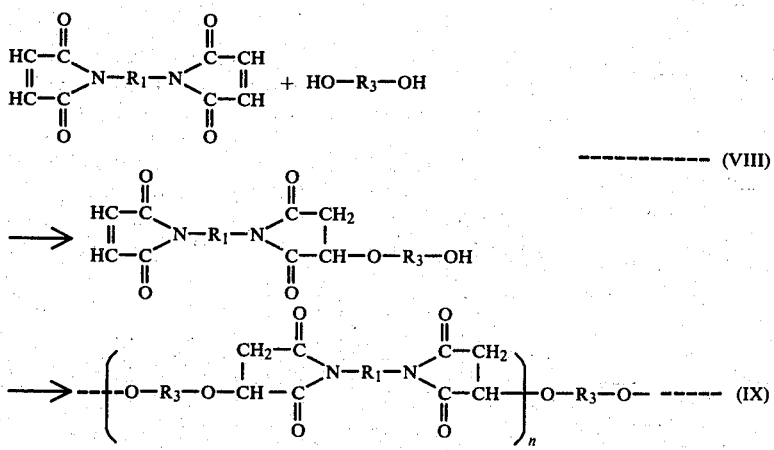

The formula (IX) shows a macromolecular structure formed by reacting or polymerizing the bismaleimide-ether compound (VIII). When the group $R_3$ contains one or more hydroxy groups, the hydroxyl groups react with carbon-carbon double bonds of maleimide groups to form a net-work structure.

(8) Applications and modifications

The bisimide-ether compound or resin and resin compositions containing the same are particularly useful for electrical insulating material because of its excellent heat resistant properties. Since the polymer and compositions are good in solubility to low-boiling-point organic solvents, they are useful as varnish for impregration, coating and casting, powder for molding, adhesives, laminates, prepregs and others.

When the compound and the compositions are used in the form of varnish, they are solved in a proper solvent, such as, acetone, methylethyl ketone, methylisobuty ketone, dioxane, methyl cellosolve, ethyl cellosolve and mixtures thereof. The compound or composition may, of course, be solved in high-boiling-point solvents such as N-methyl-2-pyrrolidone, N,N'-dimethylformamide. After the varnish is applied to a proper fabrics such as glass cloth, laminated glass cloth is dried. The resulting laminate is curable by heating under pressure to convert a thermoset resin having excellent heat resistant properties.

The bisimide-ether compound and the composition containing the same can be mixed with various kinds of other materials such as organic or inorganic fillers, surface treating agents (e.g. silane coupling agent), antiflame agents, mold separators, pigments, plasticisers, oxidation inhibitors, or the like.

The present invention will now be explained in detail by reference to examples in which parts are all by weight. It should be noted, however, that these examples are for the purpose of illustration of the present invention, not for limiting the scope of the present invention.

EXAMPLES AND COMPARATIVE EXAMPLES

EXAMPLE 1

| | |
|---|---|
| Maleic acid anhydride | 20 parts |
| | (0.20 mole) |
| 4,4-Methylene-bis(2-chloroaniline) | 30 parts |
| | (0.11 mole) |
| Phenel novolac resin | 50 parts |
| Softening point: 75° C., Active hydrogen | |
| (equivalent per hydroxyl group: about 100) | |

-continued

| Molecular weight: about 1000 |
|---|

The above mentioned composition was prepared and heated at 150° to 170° C. for 30 minutes to effect a fusion reaction therebetween, thereby to obtain a red, transparent, solid resin of B stage.

According to infrared spectrum, absorption at 1780 cm$^{-1}$ due to carbonyl groups of the imide rings and absorption at 1260 cm$^{-1}$ due to ether bonds in the resulting polymer were observed. The rate of cyclization of imide groups imidization was about 70% and a content of the corresponding bisimide-ether resin was 70% by weight.

The B-stage resin composition was well soluble in acetone and methylethyl ketone to form a solution of a non-volatile substance concentration of 50% or more.

After the B-stage composition was ground, 0.4 part of 2-ethyl-4-imidazole was added to the powder. The resulting mixture was then charged in a metal mold to obtain moldings under the conditions set forth in Table 1.

EXAMPLE 2

| Maleic acid anhydride | 25 parts (0.26 mole) |
|---|---|
| 4,4'-diamino-diphenylmethane | 30 parts (0.15 mole) |
| Phenol novolac resin used in Example 1 | 45 parts |

The above mentioned composition was heated at 150° to 180° C. for 20 minutes to effect a fusion reaction. By the same manner as in Example 1, molding articles were obtained. An imidization rate was 65% and a content of the corresponding bisimide-ether compound was 65% by weight. The B-stage composition was well soluble in acetone and methylethyl ketone.

EXAMPLE 3

| Maleic acid anhydride | 20 parts (0.20 mole) |
|---|---|
| 4,4'-diamino diphenol methane | 20 parts (0.10 mole) |
| Cresol novolac resin<br>  Softening point: about 80° C.<br>  Active hydrogen equivalent<br>  per hydroxyl group: about 110<br>  Molecular weight: about 1100 | 60 parts |

The mixture of the above-mentioned composition was heated at 140° to 180° C. for 30 minutes to obtain a B-stage, red, transparent polymer. A conversion rate of the mixture to a bisimide-ether compound was about 75%.

After the resulting polymer was ground, the powder was admixed with 3 parts of hexamethylene tetramine and 0.2 part of 2-methylimidazole, and then the mixture was charged in a metal mold of 180° C., and molded in the same manner as in Example 1.

EXAMPLE 4

| Maleic acid anhydride | 20 parts<br>(0.20 mole) |
|---|---|
| 4,4-Methylene bis (2-chloroaniline) | 25 parts<br>(0.09 mole) |
| Para-hydroxy polystyrene resin<br>  Softening point: about 150° C.)<br>  Hydroxyl equivalent: 120,<br>  marketed by Maruzen Sekiyu Co., | 50 parts |

-continued

| Japan under the name of "Resin-M" |
|---|

The mixture of the above-mentioned composition was heated at 150° to 180° C. for 25 minutes to obtain a B stage, orange, transparent resin. The conversion rate to bisimide-ether compound was about 75%, and a content of the bisimide-ether compound was about 75% by weight.

After grinding the resin, the resin was admixed with 1 part of hexamethylene tetramine and 0.4 part of an azine adduct of 2-ethyl-4-methyl imidazole. The mixture was molded in a 180° C. metal mold in the same manner as in Example 1.

EXAMPLE 5

| Maleic acid anhydride | 20 parts (0.20 mole) |
|---|---|
| 4,4-Diaminodiphenyl methane | 70 parts (0.36 mole) |
| Phenol novolac resin used in Example 1 | 20 parts |
| Bisphenol A | 10 parts |

The mixture was reacted to be B-stage. An imidization ratio of the reaction ingredients was 75% and a content of the corresponding bisimide-ether compound was about 75% by weight.

After grinding the B-stage resin, 0.5 part of 2-ethyl-4-methyl imidazole was added to the resin. The mixture was then molded in a 180° C. metal mold in the same manner as in Example 1.

EXAMPLE 6

| Tetrahydrophthalic acid anhydride | 30 parts (0.20 mole) |
|---|---|
| 4,4'-Methylene bis (2-chloroaniline) | 25 parts (0.09 mole) |
| Cresol novolac resin used in Example 3 | 50 parts |
| 2-methyl imidazole | 0.2 part |

The mixture of the composition was heated at 130° to 180° C. for 30 minutes to obtain a B-stage resin. The conversion rate to bisimideether polymer was about 65%.

After grinding the resin 0.5 parts of an azine adduct of 2-ethyl-4-methyl imidazole (marketed by Shikoku Kasei, Japan under the name of 2-ethyl-4-methyl imidazole-azine), was added to the power resin. The mixture was molded under the same conditions as in Example 1.

Curing characteristics (gel time) of the B-stage resins obtained in Examples 1–6 and heat-resistant properties of molded articles are shown in Tables 1 and 2.

For comparison, there are shown curing characteristics and heat-resistant properties of aminobismaleimide resin (Imide) and epoxy resin admixed with dicyanodiamide (Epoxy).

In tables, definitions are as follows:

| (1) | Flexural strength | Retention rate of flexural strength at a certain temperature to that at 20° C. |
|---|---|---|
| (2) | Flexural strength after heating | Retention rate of bending strength after heating in air at 220° C. for a certain time to the initial flexural strength. |
| (3) | Non-flammability | Non-flammability test under UL-94 was conducted. When an average flame self-extinguishing time is less than 25 seconds and the maximum self-extinguishing time is less than 30 seconds, the resins are graded as |

-continued

| | V-1. |
|---|---|
| (4) Weight decrease temperature | A temperature at which a weight of a sample starts to decrease by heating in air at a temperature of elevation speed of 4° C./min. |
| (5) Weight loss at 500° C. | A rate of weight loss at 500° C. |

TABLE 1

| Items | Examples | | | | | | Comparative Examples | |
|---|---|---|---|---|---|---|---|---|
| | 1 | 2 | 3 | 4 | 5 | 6 | 1. Imide | 2. Epoxy |
| Gel time at 180° C. (sec.) | 110 | 176 | 102 | 94 | 90 | 110 | 260 | 180 |
| Molding   Temperature (°C.) | 180 | 180 | 180 | 180 | 180 | 180 | 180 | 170 |
| conditions Time (min.) | 60 | 60 | 60 | 60 | 60 | 60 | 75 | 60 |
| After-cure Temperature (°C.) | 190 | 200 | 190 | 190 | 190 | 190 | 250 | — |
| conditions Time (min.) | 100 | 120 | 100 | 80 | 100 | 120 | 180 | — |
| Weight decrease temperature (°C.) | 403 | 410 | 395 | 400 | 405 | 403 | 405 | 340 |
| Weight loss at 500° C. (%) | 25 | 16 | 24 | 22 | 20 | 25 | 20 | 65 |

TABLE 2

| Items | | Examples | | | | | | Comparative Examples | |
|---|---|---|---|---|---|---|---|---|---|
| | | 1 | 2 | 3 | 4 | 5 | 6 | 1. Imide | 2. Epoxy |
| Flexural | 100° C. | 90 | 93 | 86 | 88 | 90 | 85 | 85 | 70 |
| strength | 150° C. | 85 | 88 | 80 | 84 | 85 | 78 | 80 | 45 |
| (%) | 180° C. | 80 | 80 | 73 | 75 | 77 | 72 | 75 | Not measurable |
| | 220° C. | 66 | 70 | 60 | 62 | 65 | 60 | 65 | " |
| Flexural | 500 hours | 100 | 100 | 100 | 100 | 100 | 100 | 100 | " |
| strength | 1000 hours | 90 | 93 | 77 | 76 | 88 | 82 | 75 | " |
| after heating | 1500 hours | 78 | 80 | 66 | 68 | 75 | 70 | 68 | " |
| (%) | 2000 hours | 64 | 67 | 60 | 62 | 65 | 62 | 58 | " |
| Non-flammability | | V-1 | V-1 | V-1 | V-1 | V-1 | V-1 | V-1 | Flammable |

EXAMPLE 7

| Maleic acid anhydride | 15 parts (0.15 mole) |
|---|---|
| 4,4'-Methylene bis (2-chloroaniline) | 20 parts (0.08 mole) |
| Cresol novolac resin used in Example 3 | 50 parts |

The mixture was heated at 150° to 180° C. for 30 minutes to obtain a composition. An imidization rate was more than 80%, and a content of bisimide-ether compound was more than 80% by weight. Thereafter, 20 parts of cresol novolac epoxy resin (epoxy equivalent 230) was admixed with the composition. The resulting mixture was molded by a metal mold under the conditions set forth in Table 3.

EXAMPLE 8

| Maleic acid anhydride | 15 parts (0.15 mole) |
|---|---|
| 4,4'-Diaminodiphenyl methane | 20 parts (0.10 mole) |
| Phenol novolac resin used in Example 1 | 50 parts |

After the mixture of the above-mentioned composition was heated at 150° to 180° C. for 20 minutes to obtain a thermosetting resin composition.

An imidization rate was about 75%, and a content of the corresponding bisimide-ether compound was about 75% by weight. The composition was well soluble in acetone and methyl ethyl ketone. Then, 30 parts of a phenol novolac type epoxy resin (epoxy equivalent: 178, DEN-438, Dow Chemical Co.) and 0.4 part of 2-ethyl-4-methylimidazole were admixed with the reaction product of the composition. The resulting mixture was molded in the same manner as in Example 7.

EXAMPLE 9

| Maleic acid anhydride | 15 parts (0.15 mole) |
|---|---|
| 4,4'-Diaminodiphenyl methane | 40 parts (0.20 mole) |
| Phenol novolac resin used in Example 1 | 30 parts |

After heating the mixture of the composition at 150° to 180° C. for 30 minutes (imidization rate: 55%), 40 parts of hydantoin type epoxy resin (epoxy equivalent: 163, Ciba-Geigy Ltd.) and 0.5 part of 2-methylimidazole were admixed with the reaction product of the composition. Then, the mixture was molded.

EXAMPLE 10

| Maleic acid anhydride | 15 parts (0.15 mole) |
|---|---|
| Tetrahydrophthalic acid anhydride | 5 parts (0.03 mole) |
| 4,4'-methylene bis (2-chloroaniline) | 30 parts (0.11 mole) |
| Cresol novolac resin used in Example 3 | 30 parts |

After heating the mixture of the composition at 150° to 175° C. for 25 minutes (imidization rate: 55%), the resulting reaction product was mixed with 10 parts of hydantoin type epoxy resin used in Example 9, 20 parts of phenol novolac epoxy resin used in Example 8, and 0.4 part of 2-ethyl-4-methylimidazole. The mixture was further reacted by heating for 5 minutes. The resulting B-stage resin was molded.

EXAMPLE 11

| Maleic acid anhydride | 10 parts (0.10 mole) |
|---|---|
| 4,4'-diaminodiphenyl methane | 30 parts (0.15 mole) |
| Phenol novolac resin used in Example 1 | 20 parts |
| Bisphenol-A | 10 parts |

After the mixture was heated at 150° to 175° C. for 30 minutes (imidization rate: 75%), 20 parts of hydantoin type epoxy resin used in Example 9, 20 parts of brominated bisphenol A type epoxy resin (epoxy equivalent: 455, DER-511, Dow Chemical Co.), and 0.4 part of 2-ethyl-4-methylimidazole were mixed with the reaction product. The mixture was molded in the same manner as in previous examples.

Curing characteristics (gel time) of the compositions prepared in Examples 7-11 and heat-resistant properties of the molding articles of Examples 7-11 are shown in Table 3.

TABLE 3

| Items | | Examples | | | | |
|---|---|---|---|---|---|---|
| | | 1 | 2 | 3 | 4 | 5 |
| Gel time at 180° C. (sec.) | | 160 | 75 | 82 | 72 | 80 |
| Molding conditions | Temperature (°C.) | 180 | 180 | 180 | 180 | 180 |
| | Time (min.) | 60 | 60 | 60 | 60 | 60 |
| After-cure conditions | Temperature (°C.) | 190 | — | — | — | — |
| | Time (min.) | 50 | — | — | — | — |
| Weight decrease temperature (°C.) | | 396 | 390 | 392 | 394 | 374 |
| Weight loss at 500° C. (%) | | 24 | 28 | 30 | 32 | 32 |
| Flexural strength (%) | 100° C. | 85 | 84 | 82 | 84 | 82 |
| | 150° C. | 78 | 73 | 70 | 74 | 70 |
| | 180° C. | 74 | 70 | 68 | 70 | 66 |
| | 220° C. | 63 | 60 | 58 | 57 | 57 |
| Flexural strength after heating (%) | 500 hours | 100 | 100 | 100 | 100 | 100 |
| | 1000 hours | 85 | 84 | 82 | 83 | 80 |
| | 1500 hours | 72 | 770 | 68 | 70 | 66 |
| | 2000 hours | 60 | 56 | 52 | 55 | 50 |
| Non-flammability | | V-1 | V-1 | V-1 | V-1 | V-0 |

In table, V-O designates the non-flammability that in the non-flammability test under UL-94, the average flame extinguishing time is less than 5 seconds and the maximum extinguishing time is less than 10 seconds.

EXAMPLE 12

| N,N'-methylene di-p-phenylene dimaleimide | 60 parts |
|---|---|
| Phenol novolac resin used in Example 1 | 40 parts |

The mixture of the composition was heated at 150° C. for 30 minutes to effect fusion reaction to thereby obtain a red, transparent, solid resin of B-stage. A content of the corresponding bisimide-ether compound which is well soluble in acetone and methyl ethyl ketone was more than 80% by weight.

EXAMPLE 13

| N,N'-methylene di-p-phenylene dimaleimide | 60 parts |
|---|---|
| Resol type phenol resin (Hydroxyl equivalent: about 105 Softening point: about 70°C., Hitachi Chemical Co., Ltd) | 40 parts |

The mixture was heated at 130° C. for 10 minutes to obtain a red, transparent, solid resin of B-stage. A content of the corresponding bisimide-ether compound was more than 80% by weight.

EXAMPLE 14

| N,N'-methylene bis(3,4-dichlorophenylene) dimaleimide | 50 parts |
|---|---|
| Phenol novolac resin used in Example 1 | 35 parts |

After the mixture was reacted at 150° C. for 20 minutes, the reaction temperature was lowered to 130° C. at which 5 parts of 4,4'-methylene bis (2-chloroaniline) was admixed with the reaction product. Then, the resulting mixture was heated to effect fusion reaction to obtain a red, transparent, solid resin of B-stage. A content of the corresponding bisimide-ether compound was more than 80% by weight.

EXAMPLE 15

| N,N'-methylene bis(3,4-dichlorophenylene) dimaleimide | 50 parts |
|---|---|
| Para-hydroxypolystyrene resin used in Example 4 | 50 parts |

The mixture was heated at 160° C. for 30 minutes to obtain an orange, solid resin of B-stage. A content of bisimide-ether compound was more than 80%.

EXAMPLE 16

| N,N'-methylene-p-phenylene dimaleimide | 50 parts |
|---|---|
| Phenol novolac resin used in Example 1 | 35 parts |

After heating the mixture at 150° C. for 20 minutes, the reaction temperature was lowered to 135° C. to admix 5 parts of 4,4'-methylenedianiline. The resulting mixture was heated at 135° C. for 15 minutes to obtain a red, transparent, solid resin of B-stage. A content of bisimideether compound was more than 80%.

The B-stage resins prepared in Examples 12-16 were subjected to solubility tests in which acetone, methyl ethyl ketone (MEK), and N-methyl-2 pyrrolidone (NMP) were used as solvents. For comparison, solubility of bismaleimides used in Examples 12-16 are shown in Table 4.

TABLE 4

| | Solvents | | |
|---|---|---|---|
| | Acetone | MEK | NMP |
| Example 12 | O | O | O |
| Example 13 | O | O | O |
| Example 14 | O | O | O |
| Example 15 | O | O | O |
| Example 16 | O | O | O |
| Bismaleimide of Ex. 12 | X | X | X |
| Bismaleimide of Ex. 13 | X | X | X |
| Bismaleimide of Ex. 14 | X | X | X |
| Bismaleimide of Ex. 15 | X | X | X |
| Bismaleimide of Ex. 16 | X | X | X |

In Table 4, O designates that the resin is soluble in a solvent to form a solution of a concentration of 50% or more, and X designates that the resin is soluble in a solvent to form a solution of a concentration of 10% or less.

The resins prepared in Examples 12-16 were molded under the conditions set forth in Table 5. The heat-resistant properties of the molded articles are shown in Table 5.

TABLE 5

| Items | | Examples | | | | |
|---|---|---|---|---|---|---|
| | | 12 | 13 | 14 | 15 | 16 |
| Gel time (sec.) at 180° C. | | 240 | 140 | 200 | 320 | 160 |
| Molding conditions | Temperature (°C.) | 180 | 180 | 180 | 180 | 180 |
| | Time (min.) | 60 | 60 | 60 | 60 | 60 |
| After-cure conditions | Temperature (°C.) | 200 | 200 | 200 | 200 | 200 |
| | Time (min.) | 120 | 120 | 120 | 120 | 120 |
| Weight decrease temperature (°C.) | | 405 | 390 | 400 | 395 | 405 |
| Weight loss at 500° C. (%) | | 30 | 35 | 26 | 30 | 20 |
| Flexural | 100° C. | 85 | 80 | 90 | 80 | 85 |

TABLE 5-continued

| Items | | Examples | | | | |
|---|---|---|---|---|---|---|
| | | 12 | 13 | 14 | 15 | 16 |
| strength | 150° C. | 80 | 75 | 80 | 76 | 82 |
| (%) | 180° C. | 73 | 70 | 72 | 70 | 75 |
| | 220° C. | 60 | 56 | 60 | 58 | 65 |
| Flexural | 500 hours | 100 | 100 | 100 | 100 | 100 |
| strength | 1000 hours | 84 | 80 | 85 | 82 | 85 |
| after | 1500 hours | 70 | 68 | 73 | 67 | 74 |
| heating (%) | 2000 hours | 58 | 56 | 55 | 54 | 60 |

EXAMPLE 17

| | |
|---|---|
| N,N'-methylene di-p-phenylene bismaleimide | 60 parts |
| Phenol novolac resin used in Example 1 | 40 parts |

The mixture was heated at 150° C. for 30 minutes to effect fusion reaction to thereby obtain a red, transparent, solid resin of B-stage. The resulting resin was soluble in low boiling point solvents i.e. acetone and methyl ethyl ketone to form a solution of more than 50% concentration. While the bismaleimide can form only a 4 to 5% by weight concentration solution in the solvents.

After grinding the reaction product, 0.4 part of 2-ethyl-4-methyl imidazole was added to the powder resin. The mixture was molded by a 180° C. metal mold.

EXAMPLE 18

Instead of 2-ethyl-4-methyl imidazole in Example 18, 1.0 part of an azine adduct of 2-methylimidazole used in Example 6 was mixed with the powder resin.

EXAMPLE 19

| | |
|---|---|
| N,N'-methylene bis(3-chloro-p-phenylene) bismaleimide | 50 parts |
| Phenol novolac resin used in Example 1 | 50 parts |

The mixture of the above mentioned composition was heated at 150° C. for 30 minutes to obtain a red, transparent, solid resin of B-stage. The resin were soluble in MEK and acetone to form a solution of a resin concentration of 50% by weight or more. The bismaleimide used could form a 6 to 8% concentration solution with the solvents.

After grinding the resin, 1.2 parts of an azine adduct of 2-ethyl-4-methyl-imidazole used in Example 6 was added to the powder resin. Then, the mixture was molded by a 180° C. metal mold.

EXAMPLE 20

| | |
|---|---|
| N,N'-methylene bis(3-chloro-p-phenylene) bismaleimide | 50 parts |
| Para-hydroxypolystyrene resin used in Example 4 | 30 parts |

After the mixture of the above composition was heated at 150° C. for 20 minutes, 5 parts of 4,4'-methylene bis(2-chloroaniline) was added to the reaction product. The mixture was further reacted for 10 minutes to obtain an organe, transparent, solid resin of B-stage. The solid resin was soluble in acetone and methylethyl ketone to form a solution of 50% or more concentration.

The B-stage resin was ground and admixed with 0.3 part of 2-ethyl imidazole, and the mixture was molded.

EXAMPLE 21

| | |
|---|---|
| N,N'-methylene di-p-phenylene bismaleimide | 50 parts |
| Phenol novolac resin used in Example 1 | 45 parts |
| Azine adduct of 2-ethyl-4-methyl imidazole used in Example 6 | 0.05 part |

The mixture of the above composition was heated at 140° C. for 20 minutes to effect fusion reaction thereby to obtain a red, transparent, solid resin of B-stage. The solid resin was well soluble in acetone and methyl ethyl ketone as the resins of Examples 12-16, while the bisimide used showed poor solubility to the solvents (i.e. solution of 4 to 5% concentration).

After grinding the resulting resin, 0.3 part of 2-ethyl-4-methylimidazole was added thereto, and the mixture was molded by a metal mold kept at 180° C.

EXAMPLE 2

| | |
|---|---|
| N,N'-oxy-di-p-phenylene bismaleimide | 50 parts |
| Cresol novolac resin used in Example 3 | 50 parts |
| 2-Methylimidazole | 0.2 part |

The mixture of the above composition was molded by a metal mold kept at 180° C.

Gel times of the B-stage resins prepared in Examples 17-22 and mechanical and heat resistant properties of the molded articles are shown in Tables 6 and 7.

In Tables 6 and 7, the weight decrease temperature was measured by thermo-analysis in which a temperature was elevated at a rate of 5° C./min. In Examples 23-28 of Tables 6 and 7, compositions thereof correspond to those of Examples 17-22, except that the Examples 23-28 contain no imidazole compounds.

TABLE 6

| Items | | Examples | | | | | |
|---|---|---|---|---|---|---|---|
| | | 17 | 18 | 19 | 20 | 21 | 22 |
| Gel time at 180° C. (sec.) | | 76 | 90 | 95 | 85 | 70 | 80 |
| Molding | Temperature (°C.) | 180 | 180 | 180 | 180 | 180 | 180 |
| conditions | Time (min.) | 60 | 60 | 60 | 60 | 60 | 60 |
| After-cure | Temperature (°C.) | 200 | 200 | 200 | 200 | 200 | 200 |
| conditions | Time (min.) | 50 | 50 | 50 | 50 | 50 | 50 |
| Weight decrease temperature (°C.) | | 407 | 410 | 400 | 400 | 406 | 402 |
| Weight loss at 500° C. (%) | | 30 | 25 | 32 | 26 | 27 | 30 |
| Flexural | 100° C. | 85 | 84 | 86 | 87 | 88 | 85 |
| strength | 150° C. | 80 | 80 | 76 | 81 | 80 | 78 |
| (%) | 180° C. | 76 | 77 | 70 | 70 | 72 | 70 |
| | 220° C. | 63 | 66 | 58 | 62 | 64 | 62 |
| Flexural | 500 hours | 100 | 100 | 100 | 100 | 100 | 100 |

TABLE 6-continued

| Items | | Examples | | | | | |
|---|---|---|---|---|---|---|---|
| | | 17 | 18 | 19 | 20 | 21 | 22 |
| strength | 1000 hours | 88 | 90 | 85 | 88 | 90 | 78 |
| after heating | 1500 hours | 74 | 76 | 70 | 74 | 72 | 70 |
| (%) | 2000 hours | 60 | 65 | 55 | 56 | 60 | 52 |
| Non-flammibility | | V-0 | V-0 | V-0 | V-0 | V-0 | V-0 |

TABLE 7

| Items | | Examples | | | | | |
|---|---|---|---|---|---|---|---|
| | | 23 | 24 | 25 | 26 | 27 | 28 |
| Gel time at 180° C. (sec.) | | 240 | 240 | 280 | 300 | 230 | 300 |
| Molding | Temperature (°C.) | 180 | 180 | 180 | 180 | 180 | 180 |
| conditions | Time (min.) | 60 | 60 | 60 | 60 | 60 | 60 |
| After-cure | Temperature (°C.) | 200 | 200 | 200 | 200 | 200 | 200 |
| conditions | Time (min.) | 120 | 120 | 160 | 160 | 120 | 150 |
| Weight decrease temperature (°C.) | | 405 | 405 | 390 | 400 | 408 | 400 |
| Weight loss at 500° C. (%) | | 30 | 30 | 33 | 28 | 26 | 32 |
| Flexural | 100° C. | 85 | 85 | 86 | 86 | 88 | 84 |
| strength | 150° C. | 80 | 80 | 74 | 78 | 82 | 78 |
| (%) | 180° C. | 73 | 73 | 68 | 70 | 75 | 70 |
| | 220° C. | 60 | 60 | 55 | 62 | 66 | 60 |
| Flexural | 500 hours | 100 | 100 | 100 | 100 | 100 | 100 |
| strength | 1000 hours | 84 | 84 | 85 | 86 | 88 | 75 |
| after heating | 1500 hours | 70 | 70 | 70 | 74 | 70 | 68 |
| (%) | 2000 hours | 58 | 58 | 56 | 57 | 58 | 51 |
| Non-flammability | | V-0 | V-0 | V-0 | V-0 | V-0 | V-0 |

EXAMPLE 29

| | |
|---|---|
| N,N'-4,4'-Diphenyl ether bismaleimide | 40 parts (0.11 mole) |
| Phenol novolac resin used in Example 1 | 60 parts |
| Phenol novolac epoxy resin used in Example 8 | 20 parts |

The mixture of the above composition was heated at 180° C. for 15 minutes and charged in a metal mold of 180° C. The mixture was heated at that temperature for 60 minutes and then heated at 200° C. for 60 minutes to cure the resin.

EXAMPLE 30

| | |
|---|---|
| N,N'-4,4'-Diphenyl methane bismaleimide | 40 parts (0.11 mole) |
| Phenol novolac resin used in Example | 60 parts |

The mixture was heated at 150° C. for 30 minutes to effect reaction therebetween to thereby obtain a red, transparent, solid resin of B-stage. The solid resin was ground. The resin was well soluble in methyl ethyl ketone to form a solution containing 50% or more of resin.

The powder resin 100 parts were mixed with 200 parts of cresol novolac epoxy resin (epoxy equivalent 230, ENC-1280, marketed by Ciba-Greigy Ltd.) and 0.4 part of 2-methylimidazole. The resulting mixture was molded by a 180° C. metal mold under heating for 60 minutes.

EXAMPLE 31

| | |
|---|---|
| N,N'-4,4'-diphenyl methane bismaleimide | 40 parts (0.11 mole) |
| Cresol novolac resin used in Example 3 | 60 parts |

The mixture was heated at 150° C. for 20 minutes to effect fusion reaction. The resulting resin was mixed with 20 parts of bisphenol A type epoxy resin (epoxy equivalent 188, Epicote 828, Shell Oil Co.), and the mixture was heated at 150° C. for 10 minutes. Then, the resulting reaction product was admixed with 0.2 part of 2-ethyl-4-methylimidazole to obtain a desired B-stage resin composition.

The composition thus prepared was well soluble in acetone and methyl ethyl ketone to form a solution containing more than 50% of the composition. The resulting B-stage resin was molded in a metal mold kept at 180° C. for 80 minutes.

EXAMPLE 32

| | |
|---|---|
| N,N'-3,3'4,4'-dichlorodiphenyl methane bismaleimide | 40 parts (0.99 mole) |
| Cresol novolac resin used in Example 3 | 40 parts |

After reacting the mixture at 140° C. for 20 minutes, 40 parts of hydantoin epoxy resin (epoxy equivalent 163, XB-2818, Ciba-Geigy Ltd.) was admixed with the resin, and the mixture was reacted at 140° C. for 20 minutes to obtain a B-stage resin. The resulting resin was well soluble in methyl ethyl ketone.

After grinding the B-stage resin, 5 parts of 4,4'-diaminodiphenyl methane was mixed with the powder resin. The mixture was molded in a 180° C. metal mold for 60 minutes.

EXAMPLE 33

| | |
|---|---|
| N,N'-4,4'-diphenyl methane bismaleimide | 40 parts (0.11 mole) |
| Phenol novolac resin active hydrogen equivalent per hydroxyl group: about 90 softening point: about 80° C., Hitachi Chemical Co., Ltd., Japan | 60 parts |

The mixture of the above composition was heated at 150° C. for 30 minutes to effect fusion reaction, to thereby obtain a red, transparent solid resin. The resulting resin could easily be dissolved in acetone and methyl ethyl ketone.

After grinding the resin, 10 parts of cresol novolac epoxy resin used in Example 30, 10 parts of brominated epoxy resin of bisphenol A type and 1.2 parts of 2-methyl imidazole were mixed with the powder resin. The mixture was molded in a 180° C. metal mold for 60 minutes.

TABLE 8

| Items | | Examples | | | | |
|---|---|---|---|---|---|---|
| | | 29 | 30 | 31 | 32 | 33 |
| Gel time at 180° C. (sec.) | | 180 | 56 | 78 | 74 | 58 |
| Molding conditions | Temperature (°C.) | 180 | 180 | 180 | 180 | 180 |
| | Time (min.) | 60 | 60 | 80 | 60 | 60 |
| After-cure conditions | Temperature (°C.) | 200 | — | — | — | — |
| | Time (min.) | 600 | — | — | — | — |
| weight decrease temperature (°C.) | | 402 | 395 | 398 | 405 | 380 |
| Weight loss at 500° C. (%) | | 32 | 28 | 30 | 23 | 35 |
| Flexural strength (%) | 100° C. | 86 | 84 | 83 | 90 | 88 |
| | 150° C. | 75 | 78 | 76 | 83 | 80 |
| | 180° C. | 70 | 74 | 70 | 77 | 73 |
| | 220° C. | 62 | 60 | 65 | 60 | 58 |
| Flexural strength after heating (%) | 500 hours | 100 | 100 | 100 | 100 | 100 |
| | 1000 hours | 86 | 82 | 80 | 88 | 75 |
| | 1500 hours | 75 | 73 | 72 | 77 | 66 |
| | 2000 hours | 64 | 64 | 65 | 63 | 56 |
| Non-flammability | | V-1 | V-1 | V-1 | V-1 | V-0 |

There are shown in Table 8 curing characteristics (gel time) of the B-stage resins prepared in Examples 29–33 and heat-resistant properties of cured articles obtained in Examples 29–33.

EXAMPLE 34

| | |
|---|---|
| N,N'-4,4'-diphenyl methane bismaleimide | 40 parts |
| Phenol novolac resin used in Example 1 | 60 parts |
| 2-methyl imidazole | 0.5 part |

The mixture was heated at 130° C. for 20 minutes to obtain a red, transparent B-stage resin.

EXAMPLE 35

| | |
|---|---|
| N,N'-hexamethylenedimaleimide | 70 parts |
| Para-hydroxyl polystyrene resin used in Example 4 | 30 parts |
| 4,4'-diaminodiphenylmethane | 5 parts |

The mixture was heated at 150° C. for 30 minutes to obtain an orange, transparent B-stage resin.

EXAMPLE 36

| | |
|---|---|
| N,N'-4,4'-diphenylmethane bismaleimide | 70 parts |
| Bisphenol A | 30 parts |
| 3-Methyl imidazole | 0.5 part |

The mixture was heated at 130° C. for 25 minutes to obtain a red, transparent B-stage resin.

The resins prepared in Examples 34–36 were well soluble in acetone, methyl ethyl ketone as well as in N-methyl-2-pyrrolidone.

The resins of B-stage showed gel times set forth in Table 8 and cured articles of the resins of Examples 34–36 showed heat resistant properties set forth in Table 9.

TABLE 9

| | | Examples | | |
|---|---|---|---|---|
| | | 34 | 35 | 36 |
| Gel time at 180° C. (sec.) | | 150 | 200 | 170 |
| Molding conditions | Temperature (°C.) | 180 | 180 | 180 |
| | Time (min.) | 60 | 60 | 60 |
| After-cure conditions | Temperature (°C.) | 200 | 200 | 200 |
| | Time (min.) | 60 | 120 | 60 |
| Weight decrease temperature (°C.) | | 400 | 405 | 415 |
| Weight loss at 500° C. (%) | | 35 | 26 | 20 |

COMPARATIVE EXAMPLE 3

In order to compare the present invention with the compositions disclosed in Japanese laid-open print No. 51499 of 1977 (published Apr. 25, 1977), the following experiments were conducted.

| | |
|---|---|
| (1) N,N'-methylene bis(N-phenyl maleimide) | 1 mole |
| m-aminophenol | 2 moles |

The mixture was dissolved by heating at 120° C. for 1 hour to obtain an adduct. The adduct was raised at 220° C. for 2 hours to cure the composition, but not cured. It was found by infrared absorption analysis that the adduct contained no ether bonds and contained NH groups.

| | |
|---|---|
| (2) N,N'-methylene bis(N-phenyl maleimide) | 1 mole |
| p-aminophenol | 0.3 mole |

The mixture was heated under the same conditions mentioned above, but the resulting resin included a lot of cracks therein.

(3) The mixture of above (1) and Epicote-828 (Trade name of Shell Oil Co., USA) were mixed at a ratio, by weight, of 50:50. A laminated product of glass cloth in which the above mixture was impregnated showed a flame extinguishing time of 55 to 70 seconds. Therefore, the laminate does not satisfy the grade of V-1.

(4) The mixture of above (2) and Chissonox 221 (Trade name of epoxy resin manufactured by Chisso Co., Japan) were mixed.

The laminate using the resulting mixture showed a flame extinguishing time of 25 seconds, which could satisfy the grade of V-1, but which is poorer than that of the cured article obtained in the present invention.

COMPARATIVE EXAMPLE 4

In order to compare the present invention with the compositions disclosed in Japanese laid-open print No. 145456 of 1977 (published Dec. 3, 1977), the following experiments were conducted.

| | |
|---|---|
| (1) Aniline | 93 grams (1 mole) |
| 37% Formaniline | 81 grams (1 mole) |

The mixture was heated at 80° C. for 30 minutes to obtain anhydro formaldehyde aniline. Then, 94 grams of phenol (1 mole) was added to the resultant, and the mixture was heated. After removing water from the mixture, the reactants were kept at 180° C. for 1 hour. Thereafter, unreacted aniline and phenol were evaporated in vacuum to obtain an aniline-modified phenol resin (average molecular weight: 540).

| Aniline-modified phenol resin | 100 grams |
|---|---|
| N,N'-4,4'-Diphenyl methane bismaleimide | 80 grams |

The above components were reacted at 130° C. for 30 minutes to obtain an adduct. The adduct contained NH groups but contained no ether bonds. The adduct was dissolved in methyl ethyl ketone to prepare a varnish. After the varnish was impregnated in glass cloth, the glass cloth was dried at 130° C. for 5 minutes to obtain a prepreg of a resin content of 40% by weight. Nine sheets of the prepreg and one sheet of copper foil were laminated under a pressure of 50 kg/cm² at 170° C. for 1 hour to obtain a 1.6 mm thick copper-clad laminate. The laminate was after-cured at 200° C. for 10 hours.

The laminate showed a weight decrease temperature (defined hereinbefore) of 370° C. and a weight loss at 500° C. (defined hereinbefore) of 43%.

(2) The cured resin obtained in Example 2 of the Japanese laid-open print was used in which 54 grams (0.5 mole) of cresol was used for phenol in the experiment (1) above.

The cured resin showed a weight decrease temperature of 360° C. and a weight loss at 500° C. of 52%.

The cured resins of the above experiments (1) and (2) showed that soldering heat resistant properties at 300° C. was 100 seconds, while the resins prepared according to the present invention showed that a soldering heat resistant property at 300° C. was of more than 180 seconds.

What we claim is:

1. A bisimide-ether compound having the general formula:

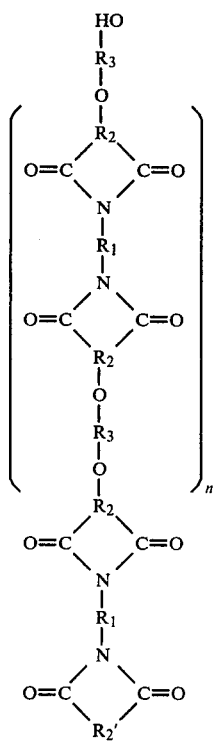

wherein $R_1$ is a group containing at least two carbon atoms, the nitrogen atoms of the imide rings being directly connected to different carbon atoms of the group $R_1$, $R_2$ is a group containing at least two carbon atoms, the carbonyl groups of the imide rings being directly connected to different carbon atoms of the group $R_2$, $R'_2$ is a group containing at least two carbon atoms and a carbon-carbon double bond, $R_3$ is an aromatic group, the oxygen atoms between the groups $R_2$ and $R_3$ being directly connected to different carbon atoms of the aromatic nucleus of the group $R_3$, and n is an integer of zero, 1 or larger than 1, the bisimide ether compound being soluble in an organic solvent having a boiling point not higher than 130° C. at normal temperature and under normal pressure.

2. A bisimide-ether compound according to claim 1, wherein $R_1$ is an aromatic group containing at least one aromatic nucleus.

3. A bisimide-ether compound according to claim 1, wherein $R_2$ is

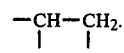

4. A bisimide-ether compound according to claim 1, wherein $R_3$ is a residue of a phenol resin having at least one free hydroxyl group directly connected to an aromatic nucleus.

5. A solvent-soluble thermosetting resin according to claim 4, wherein the phenol resin is a novolac type phenol resin polymer having a softening point lower than 170° C.

6. A method of producing a bisimide-ether compound which comprises heating a mixture of an ethylenically unsaturated dicarboxylic acid anhydride, an organic diamine and a phenolic compound containing at least two hydroxyl groups directly connected to different carbon atoms of an aromatic nucleus of the compound, said phenolic compound having a softening point lower than 170° C., at an elevated temperature for a time sufficient to provide at least 10% by weight, based on the mixture, of a bisimide-ether compound having the general formula:

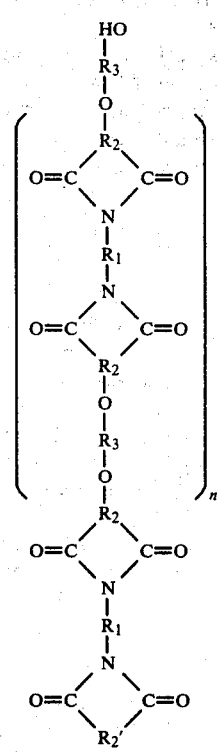

wherein $R_1$ is a residual group of the diamine containing at least two carbon atoms, the nitrogen atoms of the imide rings being directly connected to different carbon atoms of the group $R_1$, $R_2$ is a residual group of the dicarboxylic acid anhydride containing at least two carbon atoms, the carbonyl groups of the imide rings being directly connected to different carbon atoms of the group $R_2$ or $R'_2$, $R'_2$ is a group containing at least two carbon atoms and a carbon-carbon double bond, $R_3$ is a residual group of the phenolic compound, and n is an integer of zero, 1 or larger than 1, the bisimide-ether compound being soluble in an organic solvent having a boiling point lower than 130° C. at normal temperature and under normal pressure.

7. A method according to claim 6, wherein $R_1$ is an aromatic group containing at least one aromatic nucleus.

8. A method according to claim 6, wherein $R_2$ is

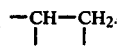

9. A method according to claim 6, wherein $R_3$ is a residue of a phenol resin and contains at least one free hydroxyl group directly connected to an aromatic nucleus.

10. A method according to claim 9, wherein the phenol resin is a novolac type phenol resin.

11. A method according to claim 6, wherein the heating of the mixture is conducted at 100° to 200° C.

12. A method according to claim 6, wherein an amount of the diamine is 0.3 to 2 mole per 1 mole of the dicarboxylic acid anhydride.

13. A method according to claim 6, wherein an amount of the phenolic compound is 30 to 70% by weight based on the mixture.

14. A method according to claim 6, wherein the heating of the mixture is conducted in the presence of 0.1 to 2% by weight, based on the mixture, of an imidazole compound.

15. A method of producing a bisimide-ether compound, which comprises heating a mixture of a bisimide represented by the general formula:

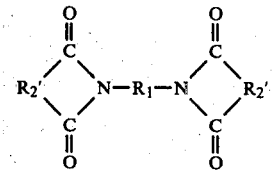

wherein $R_1$ is a group containing at least two carbon atoms, the nitrogen atoms being directly connected to different carbon atoms of the group $R_1$, and $R'_2$ is a group containing at least two carbon atoms and a carbon-carbon double bond, the carbonyl groups of the imide rings being directly connected to different carbon atoms of the group $R'_2$, and a phenolic compound having at least two hydroxyl groups directly connected to different carbon atoms of an aromatic nucleus of the phenolic compound at an elevated temperature for a time sufficient to produce at least 10% by weight, based on the mixture, of a bisimide-ether compound having the general formula:

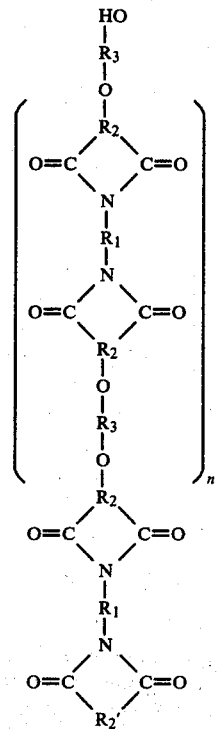

wherein $R_1$ has the same meaning as defined above, $R_2$ is a group derived from the group $R'_2$ by combining the hydroxyl groups of the phenol compound therewith, $R_3$ is a residue of the phenol compound, and n is an integer of zero, 1 or larger than 1, the bisimide-ether compound being soluble in an organic solvent having a boiling point lower than 130° C. at normal temperature and under normal pressure.

16. A method according to claim 15, wherein $R_1$ is an aromatic group containing at least one aromatic nucleus.

17. A method according to claim 15, wherein $R_2$ is

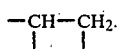

18. A method according to claim 15, wherein $R_3$ is a residue of a phenol resin and contains at least one free hydroxyl group directly connected to an aromatic nucleus.

19. A method according to claim 17, wherein the phenol resin is a novolac type phenol resin containing more than two hydroxyl groups.

20. A method according to claim 15, wherein the heating of the mixture is conducted at 100° to 200° C.

21. A method according to claim 15, wherein the heating of the mixture is conducted in the presence of an imidazole compound in an amount of 0.1 to 2% by weight based on the mixture.

22. A solvent-soluble thermosetting resin composition comprising a bisimide-ether compound having the general formula:

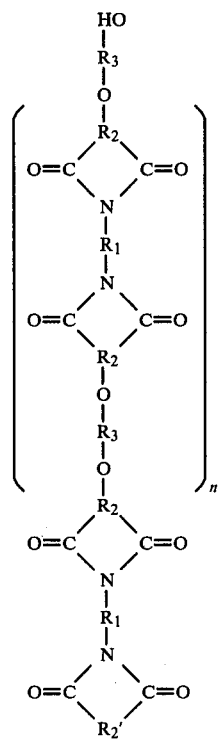

wherein $R_1$ is a group containing at least two carbon atoms, the nitrogen atoms of the imide rings being directly connected to different carbon atoms of the group $R_1$, $R_2$ is a group containing at least two carbon atoms, $R'_2$ is a group containing at least two carbon atoms and a carbon-carbon double bond, the carbonyl groups of the imide rings being directly connected to different carbon atoms of the group $R_2$ or $R'_2$, $R_3$ is an aromatic group containing at least one aromatic nucleus, the oxygen atoms between the groups $R_2$ and $R_3$ being directly connected to different carbon atoms of an aromatic nucleus, and n is an integer of zero, 1 or larger than 1, the bisimide-ether compound being soluble in an organic solvent having a boiling point lower than 130° C. and a hardener.

23. A solvent-soluble thermosetting resin composition according to claim 22, wherein $R_1$ is an aromatic group containing at least one aromatic nucleus.

24. A solvent-soluble thermosetting resin composition according to claim 22, wherein $R_2$ is

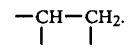

25. A solvent-soluble thermosetting resin composition according to claim 22, wherein $R_3$ is a residue of a phenol resin containing at least one free hydroxyl group directly connected to an aromatic nucleus.

26. A solvent-soluble thermosetting resin composition according to claim 25, wherein the phenol resin is a novolac type phenol resin polymer having a softening point lower than 170° C.

27. A solvent-soluble thermosetting resin composition comprising a bisimide-ether compound having the general formula:

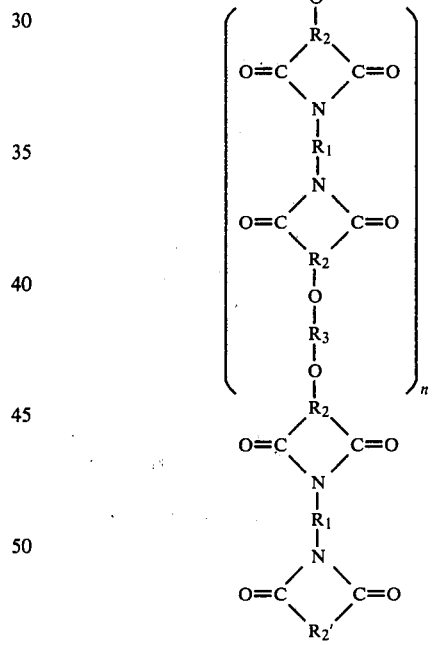

wherein $R_1$ is a group containing at least two carbon atoms, the nitrogen atoms of the imide rings being directly connected to different carbon atoms of the group $R_1$, $R_2$ is a group containing at least two carbon atoms, $R'_2$ is a group containing at least two carbon atoms and a carbon-carbon double bond, the carbonyl groups of the imide rings being directly connected to different carbon atoms of the group $R_2$ or $R'_2$, $R_3$ is an aromatic group containing at least one aromatic nucleus, the oxygen atoms between the groups $R_2$ and $R_3$ being directly connected to different carbon atoms of an aromatic nucleus, and n is an integer of zero, 1 or larger than 1, the bisimide-ether compound being soluble in an organic solvent having a boiling point lower than 130° C., and an epoxy resin having at least two epoxy groups.

28. A solvent-soluble thermosetting resin composition according to claim 27, which further contains an imidazole compound in an amount of 0.1 to 2% by weight based on the composition.

29. A solvent-soluble thermosetting resin composition according to claim 27, wherein an amount of the epoxy resin is 30 to 60% by weight based on the composition.

30. A method of producing a solvent-soluble thermosetting resin, which comprises heating, in the presence of an epoxy resin containing at least two epoxy groups, a mixture of a bisimide represented by the general formula:

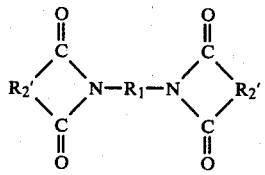

wherein $R_1$ is a group containing at least two carbon atoms, the nitrogen atoms being directly connected to different carbon atoms of the group $R_1$, and $R'_2$ is a group containing at least two carbon atoms and a carbon-carbon double bond, the carbonyl groups of the imide rings being directly connected to different carbon atoms of the group $R'_2$, and a phenolic compound containing at least two hydroxyl groups directly connected to different carbon atoms of an aromatic nucleus of the phenolic compound at an elevated temperature for a time sufficient to produce at least 10% by weight, based on the mixture, of a bisimide-ether compound having the general formula:

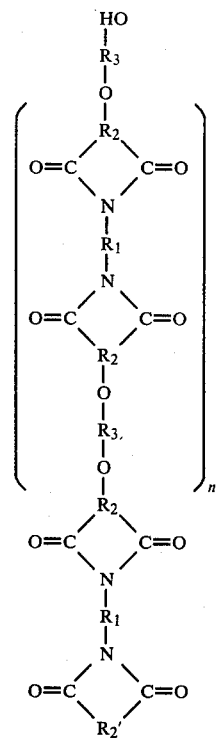

wherein $R_1$ has the same meaning as defined above, $R_2$ is a group derived from the group $R'_2$ by combining the hydroxyl groups of the phenol compound therewith, $R_3$ is a residue of the phenol compound, and n is an integer of zero, 1 or larger than 1, the bisimide-ether compound being soluble in an organic solvent having a boiling point lower than 130° C. at normal temperature and under normal pressure.

31. A method according to claim 30, wherein $R_1$ is an aromatic group having at least one aromatic nucleus.

32. A method according to claim 30, wherein $R_2$ is

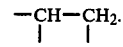

33. A method according to claim 30, wherein $R_3$ is a residue of a phenol resin and has at least one free hydroxyl group directly connected to an aromatic nucleus.

34. A method according to claim 30, wherein the phenol resin is a novolac type phenol resin having more than two hydroxyl groups.

35. A method according to claim 30, wherein the heating of the mixture is conducted at 100° to 200° C.

36. A method according to claim 30, wherein an amount of the phenolic compound is 30 to 70% by weight based on the mixture.

37. A method according to claim 30, wherein the heating of the mixture is conducted in the presence of 0.1 to 2% by weight, based on the mixture, of an imidazole compound.

38. A method according to claim 6 or claim 15 wherein n is an integer not greater than 10.

39. A method according to claim 15 or claim 30, wherein the bisimide is N,N'-4,4'-diphenylether bismaleimide; N,N'-4,4'-diphenylmethane bismaleimide or N,N'-3,3'-4,4'-dichlorodiphenylmethane bismaleimide and the phenolic compound is a phenolic novolac resin having an average number of hydroxyl groups of 3 or more or para-hydroxyl polystyrene.

40. A bisimide-ether compound according to claim 1, wherein n is an integer not greater than 10.

* * * * *